United States Patent [19]

Dubois

[11] Patent Number: 4,567,281

[45] Date of Patent: Jan. 28, 1986

[54] PREPARATION OF LACTONE-FUSED AROMATIC COMPOUNDS

[75] Inventor: Robert A. Dubois, Franklin, Mass.

[73] Assignee: The Dow Chemical Company, Midland, Mich.

[21] Appl. No.: 501,741

[22] Filed: Jun. 6, 1983

[51] Int. Cl.$^4$ .................. C07D 307/83; C07D 311/20
[52] U.S. Cl. ..................... 549/288; 549/289; 549/290; 549/310; 549/307
[58] Field of Search ............... 549/288, 289, 290, 310, 549/307

[56] References Cited

U.S. PATENT DOCUMENTS 3,462,458 8/1969 McIntyre et al. .................... 549/282
4,036,854 7/1977 Chang ................................. 549/290

OTHER PUBLICATIONS

Falbe et al., CA 62, 1558g.
Falbe, Carbon Monoxide in Organic Synthesis, Springer Verlag, N.Y., (1970), pp. 147–174.
Toshihira, CA 47, 12757i.
Matsuda, CA, vol. 69, 95586g, 1968.

*Primary Examiner*—Jane T. Fan
*Attorney, Agent, or Firm*—Norman L. Sims; Michael S. Jenkins; Christopher John Rudy

[57] ABSTRACT

This invention is a process for cyclizing an ortho-alkenyl arenol, wherein the double bond of the alkenyl moiety is one or two carbons removed from the aromatic ring, wherein the process comprises contacting an ortho-alkenyl arenol with carbon monoxide in the presence of a catalytic amount of a catalyst comprising (1) a rhodium-carbonyl complex and (2) an amine with a p$K_a$ of 6 or greater, arsine, phosphine, stibine or mixture thereof, under conditions such that a lactone-fused aromatic compound is prepared.

21 Claims, No Drawings

PREPARATION OF LACTONE-FUSED AROMATIC COMPOUNDS

BACKGROUND OF THE INVENTION

This invention relates to lactone-fused aromatic compounds and their preparation.

Lactone-fused aromatic compounds are useful in perfumes, cosmetics and as food additives.

One class of lactone-fused aromatic compounds are coumarins, which correspond to the formula

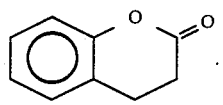

Coumarins are prepared by reacting a phenol with maleic, fumaric or acrylic acid. Also, they can be prepared by reacting salicylaldehydes with acetic anhydride or malonic acid. See Kirk-Othmer *Encyclopedia of Chemical Technology*, 3rd Ed., Vol. 7, 198–203 (1979).

Another class of lactone-fused aromatic compounds are coumar-2-ones which correspond to the formula

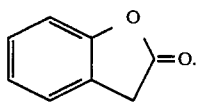

Coumaran-2-ones can be prepared by the cyclization of o-hydroxyphenylacetic acids. See Elderfield, *Heterocyclic Compounds*, Vol 2, 3 (1951).

Lactones have been prepared from unsaturated alcohols. Falbe, *Carbon Monoxide in Organic Synthesis*, Springer-Verlag N.Y., 157–158 (1967), teaches that a mixture of 5- and 6-membered ring lactones can be prepared from unsaturated alcohols when contacted with carbon monoxide in the presence of a cobalt-carbonyl or rhodium chloride catalyst at about 250° C. and about 300 atmosphere. The disclosed reaction can be described by the following equation:

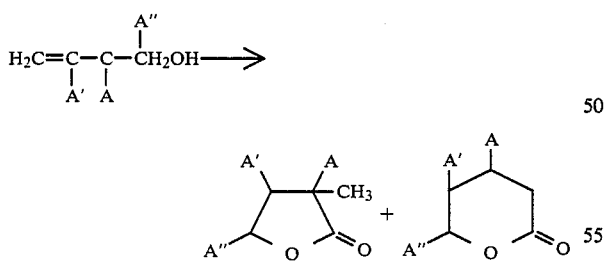

wherein A, A' and A" are hydrogen or alkyl. See also Matzuda, *Bull. Chem. Soc. Jap.*, 41(8) 1876–83 (Eng.).

What is needed is a process for the preparation of lactone-fused aromatic compounds. What is further needed is a process wherein the amount of catalyst is relatively low and the yield of the lactone-fused aromatic compounds is high. It is desirable to prepare lactone-fused aromatic compounds without using acids such as maleic acid, fumaric acid, acrylic acid, malonic acid or o-hydroxyphenylacetic acid, or using salicylaldehyde.

SUMMARY OF THE INVENTION

This invention is a process for cyclizing an ortho-alkenyl arenol, wherein the double bond of the alkenyl moiety is one or two carbons removed from the aromatic ring, with carbon monoxide, wherein such process comprises contacting an ortho-alkenyl arenol with carbon monoxide in the presence of a catalytic amount of a catalyst comprising (1) a rhodium-carbonyl complex and (2) an amine with a $pK_a$ of 6 or greater, a phosphine, arsine or stibine, or a mixture thereof, under conditions sufficient to form a lactone-fused aromatic compound.

Surprisingly, higher yields of lactone-fused aromatic compounds are achieved by this process than can be prepared by the prior art processes. Further, surprisingly smaller amounts of catalyst are used to get such yields than are used in the prior art processes.

DETAILED DESCRIPTION OF THE INVENTION

The ortho-alkenyl arenols useful in this invention include those which correspond to the formula

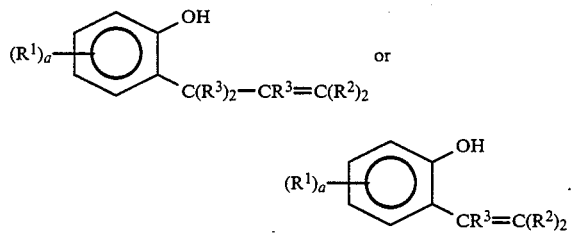

The lactone-fused aromatic compounds prepared in this invention include those corresponding to the following formula

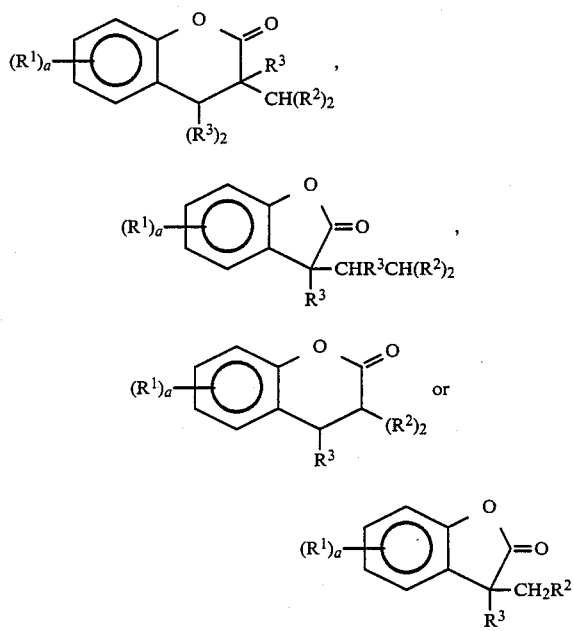

is prepared, wherein $R^1$ is separately in each occurrence halo, nitro, cyano, alkyl, aryl, alkaryl, cycloaliphatic, alkoxy; two adjacent radicals $R^1$ may together form a carbocylic 5- or 6- membered ring, or two adjacent radicals $R^1$ may combine to form one or more aromatic rings;

$R^2$ is hydrogen or alkyl;

$R^3$ is hydrogen or $C_{1-20}$ straight chained alkyl; and a is an integer from 0 to 4, inclusive.

In one embodiment of this invention an ortho-alkenyl arenol with an alkenyl moiety which has its unsaturation two carbons removed from the aromatic ring (hereinafter referred to as allylic) is reacted with carbon monoxide. This process can be better understood by reference to the following equation (I)

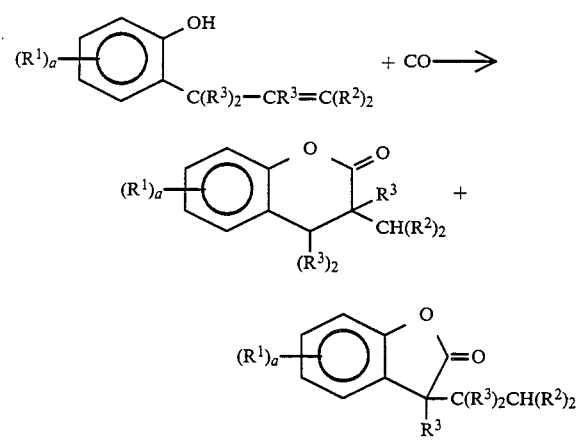

wherein $R^1$, $R^2$ and a are as defined above.

By-products can include aldehydes and alcohols produced by insertion of carbon monoxide at the point of unsaturation on the allylic group. In the above-described reaction, the mixture of major products results from the tendency of the allylic substituent to undergo isomerization to a vinylic substituent.

In another embodiment, an ortho-alkenyl arenol with an alkenyl moiety which has its unsaturation one carbon atom removed from the aromatic ring (hereinafter referred to as vinylic) is reacted with carbon monoxide. This process can better be understood by referring to the following equation (II),

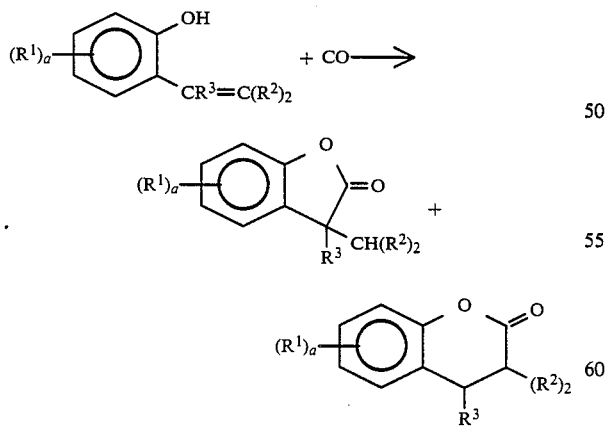

wherein $R^1$, $R^2$, $R^3$ and a are as defined above.

$R^1$ is preferably halo, nitro, cyano, alkyl, aryl, alkaryl, cycloaliphatic or alkoxy. $R^2$ is preferably lower alkyl or hydrogen and most preferably hydrogen. $R^3$ is preferably $C_{1-10}$ alkyl or hydrogen, more preferably methyl, ethyl or hydrogen, most preferably hydrogen. Preferably a is 0 or 1 and most preferably 0.

Ortho-alkenyl arenol refers to an aromatic compound which is substituted with a hydroxy moiety and further substituted with an alkenyl moiety ortho to the hydroxy moiety. Aromatic herein refers to a compound containing one or more benzene rings which can be variously substituted as described. Those compounds with more than one benzene ring can have the benzene rings fused, i.e., naphthyl, or they can be bonded together by a single bond, i.e., biphenyl, or they can be bridged by an alkylene or cycloalkylene group.

The ortho-alkenyl arenols with the ortho-vinyl or allyl groups described above include substituted phenols corresponding to the formulas

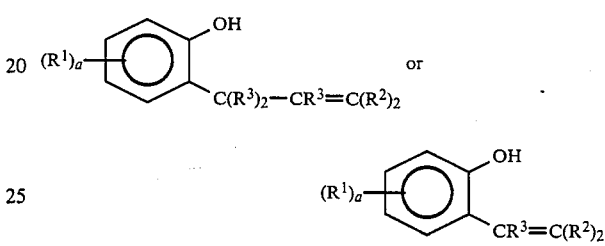

wherein $R^1$ is separately in each occurrence halo, nitro, cyano, alkyl, alkoxy, aryl; cycloaliphatic naphthols corresponding to the formulas

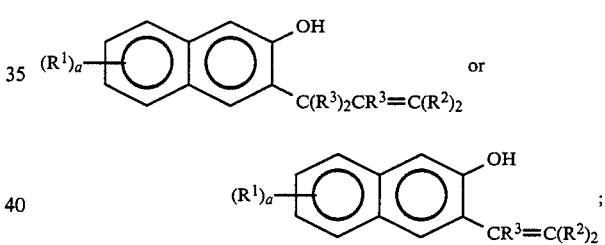

cycloalkylene-substituted phenols corresponding to the formulas

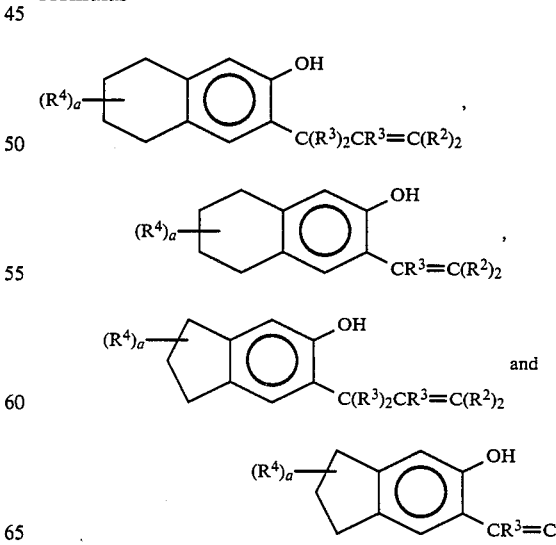

and phenylalkylene-substituted phenols corresponding to the formulas

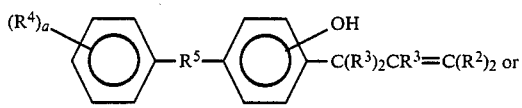

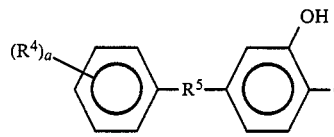

wherein R⁴ is separately in each occurrence hydroxy, cyano, nitro, halo, alkyl or aryl; R⁵ is an alkylene group; and a is an integer from 0 to 4, inclusive.

The lactone-fused aromatic compounds include fused lactone derivatives of substituted phenols which correspond to the formulas

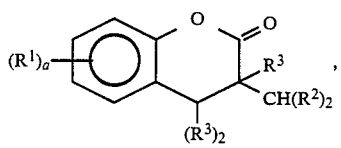

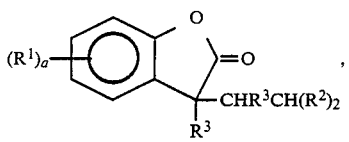

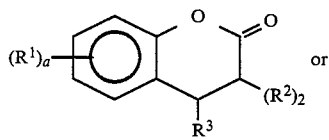

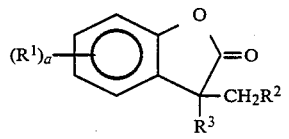

wherein R¹ is separately in each occurrence halo, nitro, cyano, alkoxy, alkyl, cycloaliphatic or aryl; fused lactone derivatives of naphthols

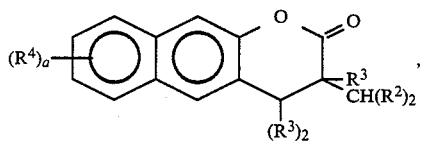

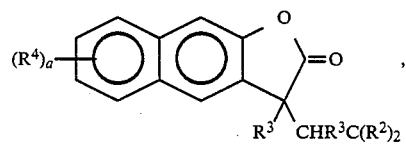

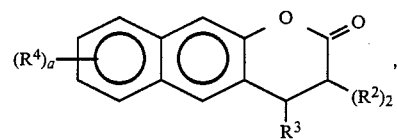

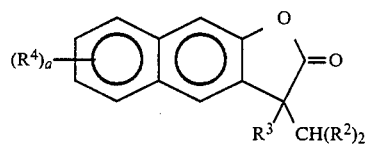

fused lactone derivatives of cycloalkylene-substituted phenols corresponding to the formulas

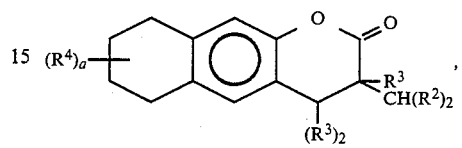

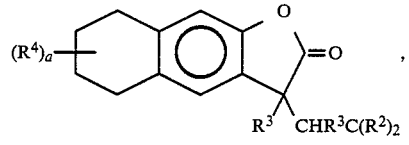

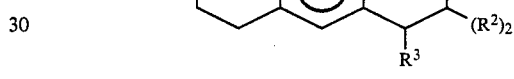

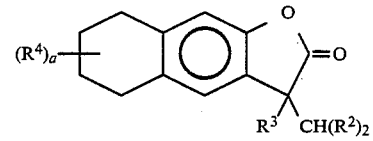

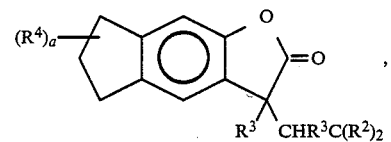

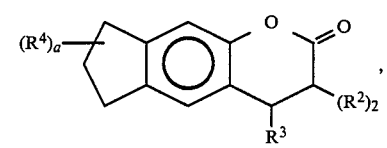

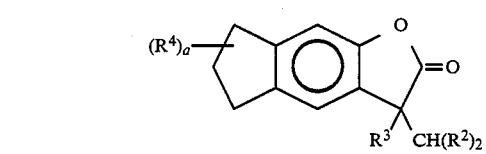

and fused lactone derivaives of phenylalkylene-substituted phenols corresponding to the formula

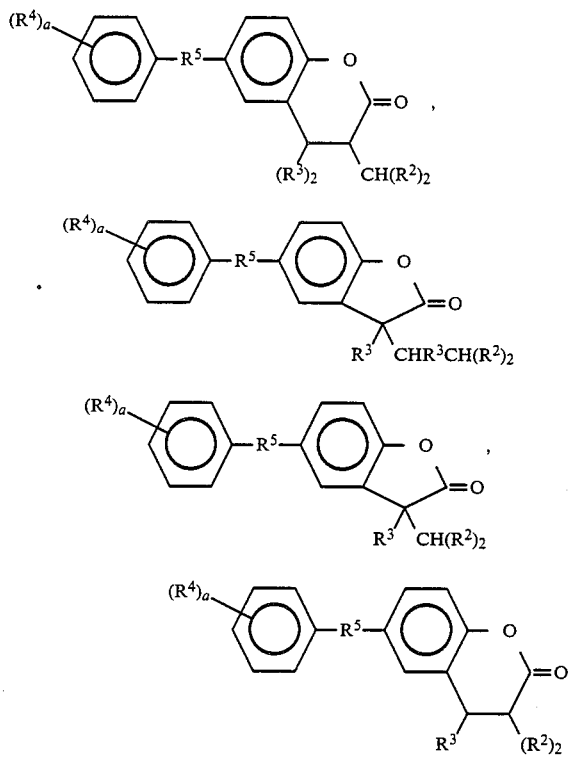

wherein $R^4$, $R^5$ and a are as defined above.

In the invented process, the ortho-alkenyl arenol dissolved in a suitable solvent is contacted with carbon monoxide in the presence of the catalyst at elevated temperatures and pressures. The presence of hydrogen gas should be avoided, as its presence leads to the formation of by-products.

The catalyst comprises (1) a rhodium-carbonyl complex and (2) an amine with a $pK_a$ of 6 or greater, a phosphine, arsine or stibine, or any mixture thereof.

The amine, phosphine, arsine or stibine may be used in the homogeneous form, or can be used in the form of a weak base anion-exchange resin wherein such a group is a pendent moiety. Unless otherwise specified, reference to amine, phosphine, arsine or stibine includes weak base anion-exchange resins which contain such groups or pendent moieties.

In a preferred embodiment, two or more of the group of an amine, phosphine, stibine or arsine are used. More preferred is a mixture of an amine and a phosphine.

The catalysts may be homogeneous or heterogeneous. A heterogeneous catalyst is preferred, as catalyst recovery is easier under such circumstances. The heterogeneous catalyst is a rhodium-carbonyl complex supported on a weak base anion-exchange resin.

In the homogeneous form, the catalyst comprises a rhodium-carbonyl complex with an amine, phosphine, arsine or stibine, or any mixture thereof.

The rhodium-carbonyl complex is prepared by exposing a rhodium-containing compound to carbon monoxide under carbonylation conditions in the presence of a small amount of a reducing agent. Carbonylation conditions suitable for preparation of the complex include high pressures, and elevated temperatures as hereinafter described. Suitable reducing agents include hydrogen gas and water. Water is preferred as hydrogen gas may affect the cyclization process detrimentally. The catalyst can be prepared prior to its use in preparing the lactone-fused aromatic compounds or it can be formed in situ. Herein in situ refers to preparing the catalyst in the presence of the reactants.

To prepare the heterogeneous catalyst, the rhodium-carbonyl complex is prepared as described above in the presence of a weak base anion-exchange resin. The heterogeneous catalyst may be prepared in situ or prior to contacting the catalyst with the reactants.

In the preparation of the rhodium-carbonyl complex, any rhodium-containing compound may be used. Examples of suitable rhodium-containing compounds include oxides such as $Rh_2O$, $Rh_2O_3$, $RhO_2$ and $RhO_3$; salts of inorganic hydracids such as rhodium chloride $RhCl_3$, rhodium bromide $RhBr_3$, rhodium iodide $RhI_3$, rhodium sulfide $Rh_2S_3$, rhodium selenide $Rh_2Se_5$ and rhodium telluride $Rh_2Te_3$; salts of inorganic oxyacids such as rhodium sulfite $Rh_2(SO_3)_3$, rhodium sulfate $Rh_2(SO_4)_3$, rhodium nitrate $Rh(NO_3)_3$, rhodium perchlorate $Rh(OH)_2ClO_4$ and rhodium selenate; salts of carboxylic acids such as rhodium acetate $Rh(CH_3CO_2)_3$ and rhodium oxalate $Rh_2(C_2O_4)_3$; and salts of heteropolyacids containing rhodium such as sodium rhodium hexachloride $Na_3[RhCl_6]$, potassium rhodium hexachloride $K_3[RhCl_6]$, barium rhodium hexachloride $Ba_3[RhCl_6]_2$, ammonium rhodium hexachloride $(NH_4)_3[RhCl_6]$, sodium rhodium hexabromide $Na_3[RhBr_6]$, monomethylammonium rhodium pentachloride $(NH_3CH_3)_2[RhCl_5]$ and trimethylammonium rhodium hexachloride $[NH(CH_3)_3]_3[RhCl_6]$.

Other derivatives which can be employed to prepare the rhodium-carbonyl complexes may furthermore include the carbonyl derivatives of rhodium such as, the compound $Rh_4(CO)_2$, $Rh_6(CO)_{16}$ and the halogenocarbonyl derivatives of rhodium such as rhodium dicarbonyl chloride $[Rh(CO_2)Cl]_2$, rhodium dicarbonyl bromide $[Rh(CO)_2Br]$ and rhodium dicarbonyl iodide $[Rh(CO)_2I]$.

Other inorganic or organic derivatives which are also suitable are the complex salts of rhodium obtained from the salts mentioned above, especially those of trivalent rhodium, and from monodentate or polydentate ligands. In this context, there may be mentioned the oxygen-containing bidentate ligands of the beta-diketone [acetylacetone] type, the nitrogen-containing monodentate ligands of the type of an alkylamine or nitrogen-containing heterocyclic compound [pyridine] and the nitrogen-containing bidentate ligands of the type of an alkyldiamine and aryldiamine or a nitrogen-containing heterocyclic base [2,2'-dipyridyl and 1,10-phenanthroline]. The bidentate ligands of the type of a diethylenic hydrocarbon of aliphatic or cycloaliphatic origin [cyclopentadiene or 1,5-cyclooctadiene] are also suitable.

As non-limiting examples of complex salts of rhodium, there may be mentioned rhodium-III acetylacetonate, rhodium trichlorotriethylamine $[RhCl_3(C_2H_5NH_2)_3]$, rhodium dichlorodiethylenediamine chloride $[RhCl_2(NH_2CH_2CH_2NH_2)_2]Cl$, rhodium triethylenediamine chloride $[Rh(NH_2CH_2CH_2NH_2)_3]Cl_3$, rhodium-III trichlorotripyridine $[RhCl_3(C_5H_5N)_3]$, rhodium-III dichlorotetrapyridine chloride $[RhCl_2(C_5H_5N)_4]Cl$, rhodium-III dichloro-didipyridyl chloride $[RhCl_2(Dipy)_2]Cl$, rhodium-III tridipyridyl chloride $[Rh(Dipy)_3]Cl_3$, rhodium-III dicyclopentadienyl nitrate $[Rh(C_5H_5)_2]NO_3$, rhodium-III dicyclopentadienyl tribromide $[Rh(C_5H_5)_2]Br_3$ and rhodium-III cyclooctadienyl chloride [Rh($C_8H_{12}$)Cl]$_3$.

Preferred rhodium-containing compounds are the carbonyl derivatives of rhodium.

Primary, secondary or tertiary amines may be used in the catalyst. Tertiary amines are preferred as the primary and secondary amines are reactive under the conditions of this process. The p$K_a$ of the amines should be 6 or greater, as little or no reaction occurs where an amine with a lower p$K_a$ is used. It is believed that as the basicity of the amine is increased, the reaction rate is increased.

Arsines comprise an arsenic atom substituted with three ligands and those useful in this process are those corresponding to the formula As(X)$_3$, wherein X is separately in each occurrence a $C_{1-20}$ hydrocarbyl moiety, preferably alkyl or aryl.

Phosphines comprise a phosphorus atom substituted with three ligands and those useful in this process correspond to the formula P(Y)$_3$ wherein Y is separately in each occurrence a $C_{1-20}$ hydrocarbyl moiety, preferably alkyl or aryl.

Stibines comprise an antimony atom substituted with three ligands and those useful in this process correspond to the formula Sb(Z)$_3$ wherein Z is separately in each occurrence a $C_{1-20}$ hydrocarbyl moiety, preferably alkyl or aryl.

Amines are the preferred species.

A weak base anion-exchange resin is a resin, exemplified by a styrene-divinylbenzene copolymer, having attached thereto a nonionic functional group or ligand exemplified by a primary amine. The weak base anion-exchange resin is not an anion-exchange resin since it does not have attached thereto an ion which can be exchanged for another ion. Weak base anion-exchange resins are characterized by the fact that they possess essentially no ion-exchange properties at pH levels greater than pH 7 as above this pH they contain no ionic group. They are composed of polymers containing primary, secondary or tertiary amines, phosphines, arsines, stilbines, thiols or sulfides. Further definition of weak base anion-exchange resins along with their preparation and properties are described in F. Helfferich, "Ion Exchange", McGraw-Hill, New York, N.Y. (1962), pp. 16, 47–58, 78, 138–40; in "Dowex Ion Exchange", The Dow Chemical Company, Midland, Mich., 1958; and in Haag et al., U.S. Pat. No. 4,111,856, incorporated herein by reference. Due to their ability in strong acid solutions to form ionic compounds with exchangeable anions, weak base resins are commonly referred to in the art as "anion-exchange resins" and specifically as "weak base anion-exchange resins". When the weak base anion-exchange resin is treated with metal compounds in the absence of strong acids, a ligand exchange can occur. No anion-exchange occurs; the metal is attached to the ligand by covalent or coordinative bonds rather than by ionic bonds. When used in this way, the anion-exchange resins would be more appropriately termed coordination resins. It is this ability of the weak base anion-exchange resins to form coordinative bonds to metals that is utilized in the present invention.

For the purposes of this invention, those weak base anion-exchange resins containing primary, secondary or tertiary amines, phosphines, arsines and stibines are useful in the process described herein. Examples of available weak base anion-exchange resins useful in this invention include: Dowex ® MWA-1, WGR and 44 (manufactured by The Dow Chemical Company); Amberlite ® IRA 45, 68 and 93 (manufactured by Rohm & Haas Company); Duolite ® A-7 and A-14 (manufactured by Diamond Alkali Company); and Ionac ® RA-260 (manufactured by Ionac Chemical Corporation).

In the embodiment wherein an amine is used as part of the catalyst, the catalyst may further comprise a phosphine of the type described above. In those embodiments wherein there is an allylic substituent ortho to the hydroxy moiety or the ortho-alkenyl arenol, the presence of the phosphine compound increases the selectivity of the reaction for the 6-membered lactone fused to the aromatic compounds over the 5-membered lactone.

Where the catalyst is homogeneous, preferable amounts of the catalyst are between about 0.2 and 10 mole percent of rhodium based upon the substrate, that is, the ortho-alkenyl arenol. More preferably, the amount is between about 2 to 6 mole percent of rhodium.

Where the catalyst is heterogeneous, it is preferable that between about 0.1 and 100 weight percent of the resin be present based upon the substrate, preferably between about 5 and 25 weight percent. Below 0.1 the reaction is very slow, the upper limit is dictated by economy. Preferably, the resin should have between about 0.1 and 20 weight percent rhodium, more preferably between 1 and 5 weight percent.

In the homogeneous process sufficient amine, phosphine, arsine or stibine should be present to afford a reasonable rate of reaction, the upper limit is determined by economy. Preferably, the amine, phosphine, arsine or stibine should be present in a mole ratio to rhodium of between about 1:1 to 100:1, preferably between about 6:1 and 50:1. Below about a 6:1 mole ratio, the reaction rate is very slow, and the isomerization of allylic substituent occurs more readily resulting in increased selectivity toward the 5-membered fused lactone.

Desirable solvents include organic nitriles such as adiponitrile, propionitrile, succinonitrile, benzonitrile, acetonitrile and the like; ketones such as methyl ethyl ketone, cyclohexanone and the like; esters such as butyl acetate, methyl formate and the like; esters such as diethyl ether, tetrahydrofuran, dioxane glycol methyl ethers and the like; chlorinated solvents such as dichloromethane, carbon tetrachloride, chlorobenzene and the like; aromatic hydrocarbons such as benzene, toluene, xylene and the like; hydrocarbons such as hexane, octane and the like; amides such as dimethylformamide and the like; sulfoxides; and sulfones. Preferable solvents are organic nitriles. The most preferable solvent is acetonitrile. The amount of solvent which is suitable is that amount which dissolves the reactants and the homogeneous catalyst if one is used. Generally, sufficient solvent to prepare a 1 molar or greater solution of the ortho-alkenyl arenol is used.

Any temperature at which the reaction occurs is suitable for this process.

Preferable temperatures are between about 25° C. and 300° C., more preferably between about 25° C. and 200° C., and most preferably between 75° C. and 150° C. Below 25° C. the reaction rate is extremely low, temperatures above 300° C. are detrimental to the reactants, products and catalyst. Temperatures between 75° C. and 150° C. afford a reasonable reaction rate without significant detriment to the reactants, products or catalyst.

The reaction pressure is preferably between 300 and 6,000 psi, and most preferably 1,000 to 3,000 psi. Below 300 psi the reaction rate is very slow, 6,000 psi is a practical upper limit based upon the ability of available equipment to handle pressure. At 1,000 psi, a reasonable rate of reaction is afforded, above 3,000 psi special equipment is required and no significant advantage is gained by using pressures above this. Usually carbon monoxide gas is used to pressurize the reaction vessel. Under such conditions, carbon monoxide is present in large excesses over the amount needed to cyclize the ortho-hydroxy compound.

This process should be run under an inert gas atmosphere, for example, nitrogen.

The reaction time can be anywhere between 1 minute and 150 hours, preferably between about 1 and 6 hours.

SPECIFIC EMBODIMENT

The following example is included for illustrative purposes only and does not limit the scope of the claims.

EXAMPLE o-Allylphenol (5.0 g, 37 mmoles), acetonitrile (25 ml) and $Rh_4(CO)_{12}$ supported on powdered Amberlite® IRA-68 (2.0 g, ~2 percent Rh) are charged under a nitrogen blanket into a glass liner which is then placed in a 300 cc magnetically driven packless Autoclave Engineers reactor. After purging with CO, the reaction is run at ~3,000 psi of Co and 135° C. for 9 hours. After cooling and venting, the contents are analyzed by capillary gas-liquid chromatography, then distilled. A fraction (2.39 g) is collected at 58° C.–70° C., 0.03 mm is 98 percent pure with a 72:28 percent mixture of 3,4-dihydro-3-methylcoumarin and 3-ethylcoumaran-2-one which corresponds to the formula

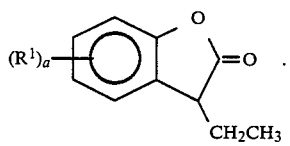

What is claimed is:

1. A process for cyclizing an ortho-alkenyl arenol, wherein the double bond of the alkenyl moiety is one or two carbons removed from the aromatic ring, with carbon monoxide, wherein the process comprises contacting an ortho-alkenyl arenol with carbon monoxide in the presence of a catalytic amount of a catalyst comprising (1) a rhodium-carbonyl complex and (2) an amine with $pK_a$ of 6 or greater, arsine, phosphine, stibine or mixture thereof, under conditions such that a lactone-fused aromatic compound is prepared.

2. The process of claim 1 wherein the ortho-alkenyl arenol corresponds to the formula

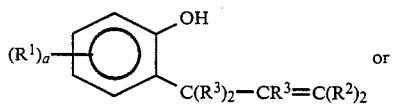
or

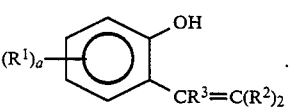

and the lactone-fused aromatic compounds correspond to the formulas

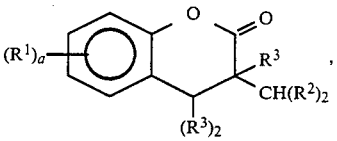

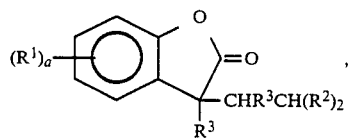

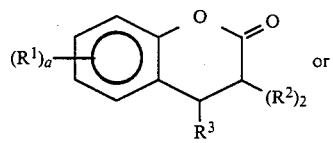
or

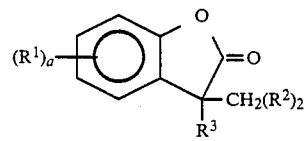

wherein $R^1$ is separately in each occurrence halo, nitro, cyano, alkyl, aryl, alkaryl, cycloaliphatic, alkoxy; two adjacent radicals $R^1$ may together form a carbocylic 5- or 6-membered ring, or two adjacent radicals $R^1$ may combine to form one or more aromatic rings; $R^2$ is hydrogen or alkyl; $R^3$ is hydrogen or $C_{1-20}$ straight chained alkyl; and a is an integer from 0 to 4, inclusive.

3. The process of claim 2 wherein the double bond on the ortho-alkenyl arenol is two carbon atoms removed from the aromatic ring and corresponds to the formula,

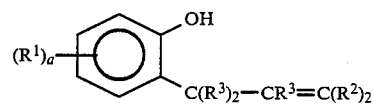

and the products are lactone-fused aromatic compounds which correspond to the formulas,

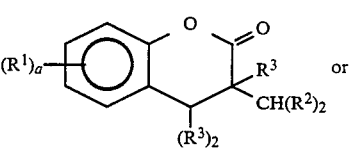
or

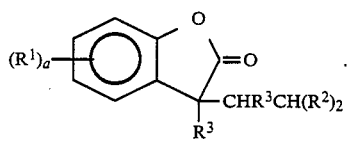

4. The process of claim 2 wherein the double bond on the ortho-alkenyl arenol is one carbon atom removed from the aromatic ring and corresponds to the formula,

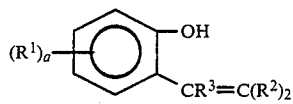

and the lactone-fused aromatic compound product corresponds to the formula,

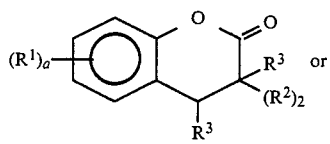

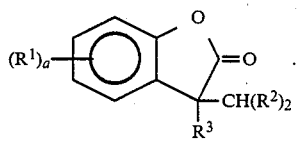

5. The process of claim 2 wherein the catalyst comprises (1) a rhodium-carbonyl complex and (2) a mixture of two of the group comprising an amine with a $pK_a$ of 6 or greater, a phosphine, a stibine or an arsine.

6. The process of claim 5 wherein the mixture comprises an amine with a $pK_a$ of 6 or greater and a phosphine.

7. The process of claim 2 wherein $R^1$ is separately in each occurrence halo, nitro, cyano, alkyl, aryl, alkaryl, cycloaliphatic or alkoxy.

8. The process of claim 2 wherein $R^2$ is hydrogen.

9. The process of claim 2 wherein a is 0 or 1.

10. The process of claim 9 wherein a is 0.

11. The process of claim 2 wherein $R^3$ is hydrogen or $C_{1-10}$ alkyl.

12. The process of claim 11 wherein $R^3$ is hydrogen, methyl or ethyl.

13. The process of claim 12 wherein $R^3$ is hydrogen.

14. The process of claim 2 wherein the catalyst comprises a rhodium-carbonyl complex and a weak base anion-exchange resin.

15. The process of claim 14 wherein the catalyst comprises a rhodium-carbonyl complex supported on a weak base anion-exchange resin.

16. The process of claim 2 wherein the temperature is between about 25° C. and 300° C.

17. The process of claim 2 wherein the temperature is between about 25° C. and 200° C.

18. The process of claim 2 wherein the temperature is between about 75° C. and 150° C.

19. The process of claim 2 wherein the pressure is between about 300 and 6,000 psi.

20. The process of claim 2 wherein the pressure is between about 1,000 and 3,000 psi.

21. The process of claim 2 wherein the amine is a tertiary amine.

* * * * *

UNITED STATES PATENT AND TRADEMARK OFFICE
CERTIFICATE OF CORRECTION

PATENT NO. : 4,567,281
DATED : January 28, 1986
INVENTOR(S) : Robert A. Dubois

It is certified that error appears in the above-identified patent and that said Letters Patent is hereby corrected as shown below:

At column 1, line 50 the formula should be typed as appears below:

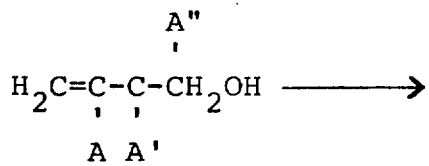

At column 2, line 68 delete the word "carbocylic" and insert therefor -- carbocyclic --.

At column 5, lines 1-5 the formula should be typed as appears below:

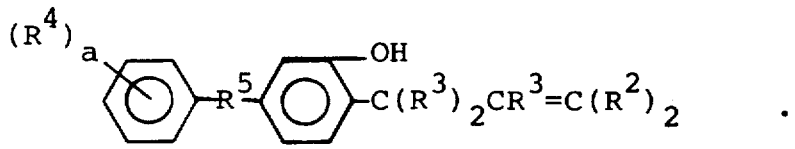

At column 6, line 66 delete the word "derivaives" and insert therefor -- derivatives --.

At column 7, line 39 delete the word "catalylst" and insert therefor -- catalyst --.

At column 10, line 44 delete the word "esters" and insert therefor -- ethers --.

At column 11, line 29 delete "Co" and insert therefor -- CO --.

At column 11, line 52 following the word "with" insert the word -- a --.

UNITED STATES PATENT AND TRADEMARK OFFICE
CERTIFICATE OF CORRECTION

PATENT NO. : 4,567,281
DATED : January 28, 1986
INVENTOR(S) : Robert A. Dubois

It is certified that error appears in the above-identified patent and that said Letters Patent is hereby corrected as shown below:

At column 12, lines 25-30 the formula should be typed as appears below:

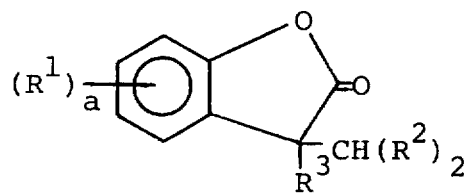

At column 12, line 32 delete the word "carbocylic" and insert therefor -- carbocyclic --.

At column 13, lines 10-15 the formula should be typed as appears below:

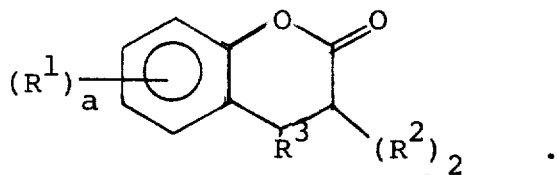

Signed and Sealed this

Thirtieth Day of September 1986

[SEAL]

Attest:

DONALD J. QUIGG

Attesting Officer　Commissioner of Patents and Trademarks